(12) United States Patent
Branemark et al.

(10) Patent No.: US 11,464,606 B2
(45) Date of Patent: Oct. 11, 2022

(54) ANCHORING SYSTEM FOR ATTACHING A PROSTHESIS TO A HUMAN BODY

(71) Applicant: INTEGRUM AB, Molndal (SE)

(72) Inventors: Rickard Branemark, Molndal (SE); Marta Bjornsdottir, Molndal (SE); Maria Lopez, Molndal (SE); Oddbjorn Hallenstvedt, Molndal (SE); Staffan Mansson, Molndal (SE)

(73) Assignee: INTEGRUM AB, Molndal (SE)

( * ) Notice: Subject to any disclaimer, the term of this patent is extended or adjusted under 35 U.S.C. 154(b) by 822 days.

(21) Appl. No.: 16/347,227

(22) PCT Filed: Nov. 7, 2017

(86) PCT No.: PCT/SE2017/051109
§ 371 (c)(1),
(2) Date: May 3, 2019

(87) PCT Pub. No.: WO2018/088950
PCT Pub. Date: May 17, 2018

(65) Prior Publication Data
US 2019/0254782 A1    Aug. 22, 2019

(30) Foreign Application Priority Data
Nov. 8, 2016 (SE) .................................... 1651462-2

(51) Int. Cl.
*A61F 2/78* (2006.01)
*A61C 8/00* (2006.01)

(52) U.S. Cl.
CPC .......... *A61C 8/0071* (2013.01); *A61C 8/0066* (2013.01); *A61F 2/78* (2013.01);
(Continued)

(58) Field of Classification Search
CPC ........................... A61F 2/78; A61F 2002/7887
See application file for complete search history.

(56) References Cited

U.S. PATENT DOCUMENTS 9,067,057 B2   6/2015  Branemark et al.
2005/0102038 A1 * 5/2005 Grundei .................... A61F 2/78
                                                      623/32

(Continued)

FOREIGN PATENT DOCUMENTS

CN      203591347 U     5/2014
DE   102008027007 A1   12/2009

(Continued)

OTHER PUBLICATIONS

International Search Report and Written Opinion for Application No. PCT/SE2017/051109, dated Jan. 4, 2018, 10 pages.

(Continued)

*Primary Examiner* — Bruce E Snow
(74) *Attorney, Agent, or Firm* — Brooks Kushman P.C.

(57) ABSTRACT

The present invention relates to an anchoring system for attaching a prosthesis to a human body, comprising: an anchoring element, an abutment, an abutment screw for attaching the abutment to the anchoring element, the anchoring element comprises a connection area for the abutment, the connection area comprising a press-fit portion such that the abutment is attached to the anchoring element in the connection area by a press-fit connection, wherein the connection area comprises an anti-rotation geometry and the abutment comprising a corresponding mating anti-rotation geometry proximal to the press-fit portion, and where in the connection area comprises a conical portion proximal to the anti-rotational geometry forming a mating geometry for a corresponding conical portion in the through-hole of the abutment.

16 Claims, 10 Drawing Sheets

(52) U.S. Cl.
CPC ..... *A61C 8/0037* (2013.01); *A61F 2002/7868* (2013.01); *A61F 2002/7875* (2013.01); *A61F 2002/7887* (2013.01)

(56) References Cited

U.S. PATENT DOCUMENTS

| | | |
|---|---|---|
| 2005/0177165 A1 | 8/2005 | Zang et al. |
| 2014/0272791 A1* | 9/2014 | Sanchez ............... A61C 8/0068 433/173 |
| 2015/0157427 A1 | 6/2015 | Purga et al. |
| 2017/0252166 A1* | 9/2017 | Bachus ................ A61F 2/2814 |

FOREIGN PATENT DOCUMENTS

| | | |
|---|---|---|
| DE | 102010051176 A1 | 5/2012 |
| EP | 1649834 A1 | 4/2006 |
| EP | 2428180 A1 | 3/2012 |
| ES | 2389543 A1 | 10/2012 |
| KR | 101240116 B1 | 3/2013 |
| WO | 9916293 A3 | 4/1999 |
| WO | 2009147255 A1 | 12/2009 |

OTHER PUBLICATIONS

Extended European Search Report for Application No. 17870014.2-1122, dated May 25, 2020, 10 pages.

\* cited by examiner

| Dimension | Symbol | Interval |
|---|---|---|
| Length of shallow thread | $L_s$ | $> 0.5L$ |
| Difference in thread depth between deep and shallow thread | $\Delta h$ | $[0.1h_d - 0.9h_d]$ or $> h_d$ |
| Length of press-fit | $L_{pf}$ | $[2 - 15]\ mm$ |
| Increased wall thickness | $t_s$ | $[1t_w - 2t_w]$ |
| Cone angle | $\theta_{cone}$ | $[0.2° - 30°]$ |
| Length of cone | $L_{cone}$ | $\geq L_c$ |
| Length of straight portion for stress-relief | $L_{st}$ | $> L_{cone}$ |

Fig. 11

ANCHORING SYSTEM FOR ATTACHING A PROSTHESIS TO A HUMAN BODY

CROSS-REFERENCE TO RELATED APPLICATION

This application is the U.S. national phase of International Application No. PCT/SE2017/051109 filed on Nov. 7, 2017, which claims priority to Sweden Patent Application No. SE 1651462-2 filed on Nov. 8, 2016, the disclosures of which are incorporated in their entirety by reference herein.

TECHNICAL FIELD

The present invention relates to an anchoring system for attaching a prosthesis to a human body.

BACKGROUND OF THE INVENTION

Generally, osseointegrated prostheses for rehabilitation of amputees (OPRA system) are known and have been developed and commercialized by Integrum AB, Mölndal, Sweden. The OPRA system is currently used to anchor limb prostheses by means of a titanium implant that is surgically inserted into the bone. Generally, the OPRA system consists of a titanium screw implanted inside the bone and which serves as a fixture for an abutment, a central screw, and the abutment which is partly inserted inside the fixture and partly exiting the bone and stump so that the attachment of the artificial limb can be arranged at the head of the abutment.

In the present OPRA system a first surgery is carried out in which the fixture is implanted in the long bone and the central screw is inserted into the fixture. During a healing period of about six months the bone growths onto the fixture to anchor it in the femur. This bone growth process is called osseointegration. After the healing period a second surgery is carried out in which the abutment is attached to the fixture. Part of the abutment extends outside the skin to allow the prosthesis to be attached. An abutment screw is then attached to lock the fixture and the abutment together.

EP 0 595 782 B1 discloses a fixture for supporting a prosthesis and is provided with a central through bore and having a slit or slits arranged in spiral form around the longitudinal axis of the fixture and extending over the major part of the threaded outside.

U.S. Pat. No. 9,067,057 B2 discloses an anchoring element for fixation in bone tissue, the anchoring element defining a longitudinal axis and comprising at least one first through-hole substantially extending in the direction the longitudinal axis. The anchoring element comprises first attachment means for attaching the anchoring element to the bone tissue and second attachment means for directly or indirectly attaching the anchoring element to a prosthetic limb. It is further described how a sealing device is adapted to be positioned in the through-hole in a sealing manner.

In Ortiz et al "An osseointegrated human machine-gateway for long-term sensory feedback and motor control of artificial limb" in Science Translational Medicine 8 Oct. 2014 Vol. 6 Issue 257 pp. 257re6 it is presented an amputee case fitted with the OPRA system. A percutaneous osseointegrated (bone-anchored) interface was used that allows for permanent and unlimited bidirectional communication with the human body. With such an interface an artificial limb can be chronically driven by implanted electrodes in the peripheral nerves and muscles of an amputee. Specifically, a hole was drilled through the abutment screw and leads were drawn between the exoprosthesis and biceps, triceps, brachialis (epimysial electrodes) and ulnar nerve (cuff electrode). Muscle activation was used to control hand (open/close), wrist (pronation/supination, extension/flexion) and elbow (extension, flexion).

Another transcutaneous implant in the field is disclosed in U.S. Pat. No. 6,843,808.

It should be understood that a critical aspect of anchoring systems is a secure bone-anchoring as well as a sufficient mechanical strength of the system in itself. Specifically, the mechanical strength of the anchoring element might be critical due to the fact that the anchoring element may have an interior pathway for communication of physical and biological signals and not designed as a solid body.

In order to protect an implant system for an external prosthetic component, such as a limb prosthesis or a prosthetic knee, from high mechanical forces and to avoid any skeletal fracture caused by an accident situation it is previously known to design separate connector devices having a built-in safety mechanism which is activated when for instance a rotational load exceeds a specific release level. See for instance OPRA ROTASAFE and OPRA AXOR systems, also developed and commercialised by Integrum AB, Molndal, Sweden, and it is also referred to U.S. Pat. No. 9,408,723 which describes such a connector device. Connector devices of this type are specifically designed to protect the implant system from the high mechanical forces caused by an (unexpected, undesired) accident situation. The function in such case should be to limit rotational forces in the centre line of the implant and bending forces when the prosthetic component (prosthetic knee or elbow for example) is natural bent to its maximum position. All amputees are likely to have overloads or fall occasionally and a complication following osseointegration is the risk of bending the abutment. If the abutment is bent or deformed following a fall, then it must be replaced. Furthermore, if the anchoring of the fixture is disturbed then there is a risk of loosening the fixture and there has to be a new surgical operation.

In U.S. Pat. No. 9,408,723 it is described a connector device with reduced outer dimensions having a main housing which includes a built-in safety mechanism to protect the implant system from high mechanical forces and to avoid any skeletal fracture caused by an overload situation and wherein the built-in safety mechanism is arranged to limit rotating forces as well as bending forces.

However, there is a need to improve the anchoring system with respect to a secure bone-anchoring and also increase the mechanical strength of the system in itself to withstand the natural all-day forces that occur. Specifically, the system should be designed in such a way that damage to the surgically implanted parts of the system due to moderate overload forces and mechanical stresses are prevented.

SUMMARY OF THE INVENTION

In view of above-mentioned and other drawbacks of the prior art, it is an object of the present invention to improve the anchoring system with respect to mechanical strength, specifically the fatigue strength, stability and robustness.

According to a first aspect of the present invention, there is provided a anchoring system for attaching a prosthesis to a human body, the anchoring system comprising: an anchoring element comprising an outer threaded profile for anchoring to bone tissue of a human body, an abutment comprising a distal portion for linking the anchoring system to an external prosthetic component, an abutment screw for attaching the abutment to the anchoring element for providing a mechanical connection between the anchoring element and the abutment, wherein, the anchoring element comprises a through-hole with an inner profile for providing a connection area for the abutment, the connection area comprising a press-fit portion in a distal portion of the connection area, the press-fit portion having an opening dimension smaller than a dimension of a press-fit portion of the abutment such that the abutment is attached to the anchoring element in the connection area by a press-fit connection, wherein the connection area comprises an anti-rotation geometry proximal to the press-fit portion, the abutment comprising a corresponding mating anti-rotation geometry proximal to the press-fit portion of the abutment configured to engage with the anti-rotation geometry of the anchoring element, and wherein the connection area comprises a conical portion proximal to the anti-rotational geometry forming a mating geometry for a corresponding conical portion of the abutment.

The present invention is based on the realization that an anchoring system has to be designed to withstand relatively high mechanical stress. For example, if the anchoring of the anchoring element (e.g. a "fixture") is disturbed then there is a risk of loosening of the fixture and a new surgical operation might be required. According to the invention the outer profiles as well as the connection area between the abutment and the fixture are adapted to provide an improved anchoring system with regards to strength, stability and robustness.

The external prosthetic component may be for example a limb prosthesis or prosthetic knee.

The through-hole is in a longitudinal distal-proximal direction of the anchoring element.

The conical portion proximal of the anti-rotation geometry may be located at the most proximal end of the abutment and is configured to provide stability and load distribution at the most proximal end of the abutment. Thereby, the conical portion of the abutment and the corresponding mating conical portion of the anchoring element provides a stable contact point at the most proximal end of the connection area of the abutment, compared to for example flat to flat surface connections. The conical portion of the abutment is configured to mate with a corresponding matching conical portion of the anchoring element. The conical portion of the anchoring element is thus a conical hole (e.g. a countersink) configured to match with the conical portion of the abutment.

A cone angle of the conical portion of the abutment and thus also of the conical hole is in the range of about 25° to 65°, for example 42°, 45°, or 48°.

The press-fit connection is configured such that the outer dimension of the press-fit portion of the abutment is slightly larger than an inner dimension of the press-fit portion of the anchoring element such that when the abutment is forced into the opening of the through-hole of the anchoring element, the abutment is mechanically fastened to the anchoring element. In other words, press-fit portion of the abutment physically interferes with the press-fit portion of the anchoring element in a way that the abutment is mechanically attached to the anchoring element.

According to an embodiment of the invention, the outer threaded profile of the anchoring element may comprise: a first thread portion with a first thread depth, and a second thread portion with a second thread depth, wherein the first thread depth is larger than the second thread depth, and wherein the first thread portion is arranged in the proximal portion of the anchoring element and the second thread portion is arranged in the distal portion of the anchoring element. The deeper threads in the proximal first portion advantageously enable an increased bone anchoring surface area. At the same time, the second thread portion with the shallower thread to enables to increase the wall thickness of the anchoring element at the second thread portion, and thus increasing the strength, of the distal portion of the anchoring element. Furthermore, the difference in thread depth also provides a means for establishing a mechanical stop when inserting the anchoring element (e.g. the fixture) in bone tissue. Further the outer profile of the anchoring element is thus designed in such a way that a secure bone-anchoring is established and maintained.

In one embodiment of the invention, the first thread portion and the second thread portion may extend over the entire total length from the proximal-most end to the distal-most end of the anchoring element. Thereby, the bone anchoring surface area and the wall thickness may be further increased. It is the combination of the first thread portion and the second thread portion that extend over the entire length of the anchoring element.

Advantageously, the second thread portion extends over a length from the distal portion to beyond the connection area. In other words, the second end portion overlaps more than the entire connection area of the anchoring element. This further improves the strength, of the distal portion of the anchoring element. The length ($L_s$) of the shallower thread may be determined by the mating geometry (e.g. the connection area) of the inner profile and covers more than the total length ($L_c$) of the mating geometry.

According to an embodiment of the invention, the though-hole is configured as a pathway for communication of physical and/or biological signals between inside and outside of the human body. Thereby, a connection with for example the nerves inside the human body may be obtained.

According to an embodiment of the invention, the press-fit portion of the connection area extends from the distal-most end of the distal portion of the anchoring element and in a proximal direction.

The press-fit portion of the connection area may for example be cylindrical.

The press-fit portion of the connection area may for example be conical. The cone angle of the conical press-fit portion is preferably in the range between 0.2° to 30°.

In one embodiment, the press-fit portion is conical and the connection area may further comprise a straight portion arranged on the distal-most part of the connection area adjacent to the conical press-fit portion. The straight portion at the distal most end of the anchoring element advantageously provides stress relief to avoid high stress singularities in the anchoring element.

The length of the straight portion may be less than the length of the conical portion.

The anti-rotation geometry advantageously has a polygon cross-section. Such a polygon cross-section may for example be hexagon, pentagon, rectangular, triangular, square etc.

The anchoring system according to the invention may be used for patients with above knee amputations due to trauma or cancer and who have rehabilitation problems with or cannot use regular artificial leg prosthesis. The system is configured to allow a prosthesis component to attach directly to the femur (thigh bone) or other types of so-called long bones in the human body.

According to another preferred embodiment of the invention the mating surfaces between the fixture and the abutment have been treated with surface treatment for enhancing the wear and fretting resistance properties of the system.

Such surface treatments may be Diamond-like-Carbon (DLC) coating, nitriding, burnishing etc.

Further features of, and advantages with, the present invention will become apparent when studying the appended claims and the following description. The skilled addressee realize that different features of the present invention may be combined to create embodiments other than those described in the following, without departing from the scope of the present invention.

BRIEF DESCRIPTION OF THE DRAWINGS

The various aspects of the invention, including its particular features and advantages, will be readily understood from the following detailed description and the accompanying drawings, in which:

FIG. 11 is a table with parameters intervals for embodiments of the invention.

DETAILED DESCRIPTION OF EMBODIMENTS OF THE INVENTION

Figure 1:
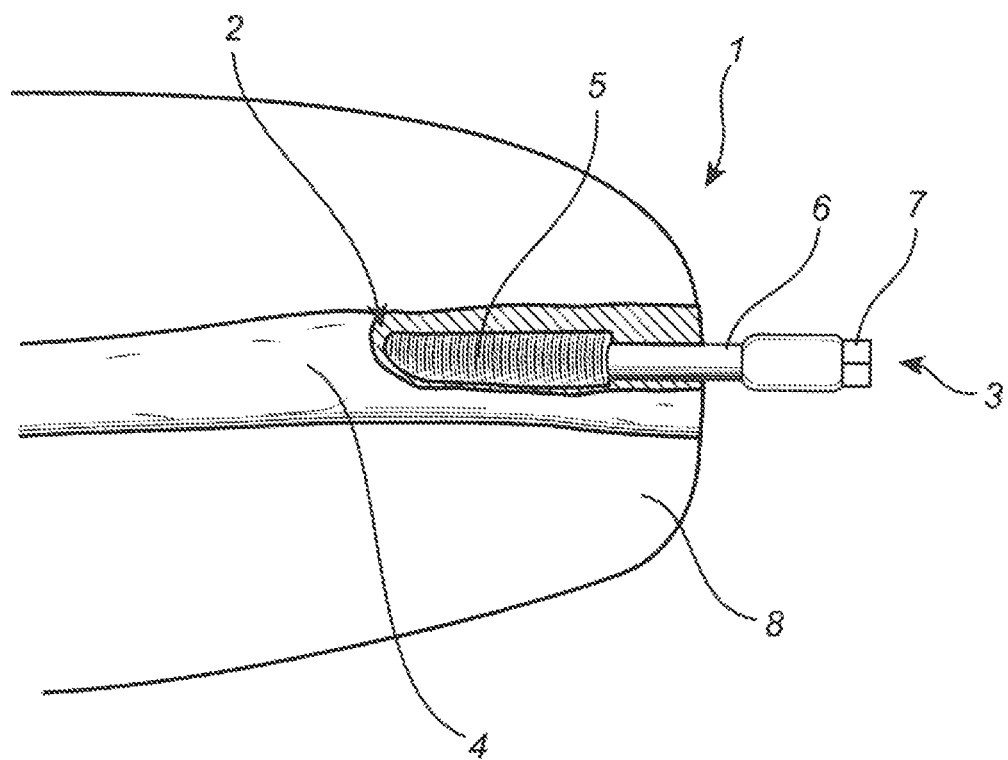
FIG. 1 is a schematic illustration of the fixation and abutment parts of a prior art anchoring system placed in the femur bone of an amputation stump.

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled person. Like reference characters refer to like elements throughout.

FIG. 1 is a schematic illustration of an anchoring system 1 placed in the femur bone 4 of an amputation stump for attaching a prosthesis. The anchoring system has a proximal end 2 and a distal end 3. The proximal end 2 of the anchoring system is anchored to the bone tissue 4 and the distal end 3 links the system to an external prosthetic component (not shown here), such as a limb prosthesis or prosthetic knee. The anchoring system 1 comprises an anchoring element 5 generally in the form of a screw (a so-called fixture) 5, an abutment 6 and an abutment screw 7 for attaching the abutment 6 to the fixture 5 thus providing the mechanical coupling between the anchoring element 5 and the abutment 6. The abutment screw 7 may be arranged through a proximal-distal through-hole of the abutment 6. However, other means of attaching the abutment to the anchoring element are possible. Further, the anchoring element 5 may have a pathway (percutaneous gateway, not shown) for communication of physical and biological signals between inside and outside of the human body. The through pathway is not shown in this figure, it is referred to for instance the U.S. Pat. No. 9,067,057 or EP 0 595 782, both which are incorporated by reference.

The external prosthetic component (not shown) is anchored to the bone by means of the anchoring element 5 that is surgically inserted into the bone 4. The anchoring element 5 is preferably completely implanted inside the bone and osseointegrated and serves as a fixture for the skin penetrating connection provided by the abutment 6. The abutment 6 is attached to the anchoring element 5 and is partly protruding out from the bone 4 and skin 8. The external prosthetic component, such as an artificial limb, is then attached at the protruding abutment part.

Bone anchored prostheses which are based on osseointegration allow a direct connection of an artificial limb prosthesis to the patients skeleton, thus avoiding the use of a socket. Osseointegrated prostheses for rehabilitation of amputees (OPRA system) have been developed and commercialized by Integrum AB, Molndal, Sweden, and will not be described in any further detail here. See also Integrum U.S. Pat. No. 9,067,057 incorporated by reference.

A typical length of a fixture 5 used in this type of prostheses is 10 mm-120 mm, partly depending on the size of the bone and partly related to the anatomy of the remaining skeleton. All parts of the system are made out of titanium or other tissue friendly/biocompatible material. As to the proximal portion of the fixture it could for instance be designed with slits, spirals and holes like illustrated in the EP 0 595 782 and U.S. Pat. No. 9,067,057 and such design will not either be described in any detail here.

Figure 2:
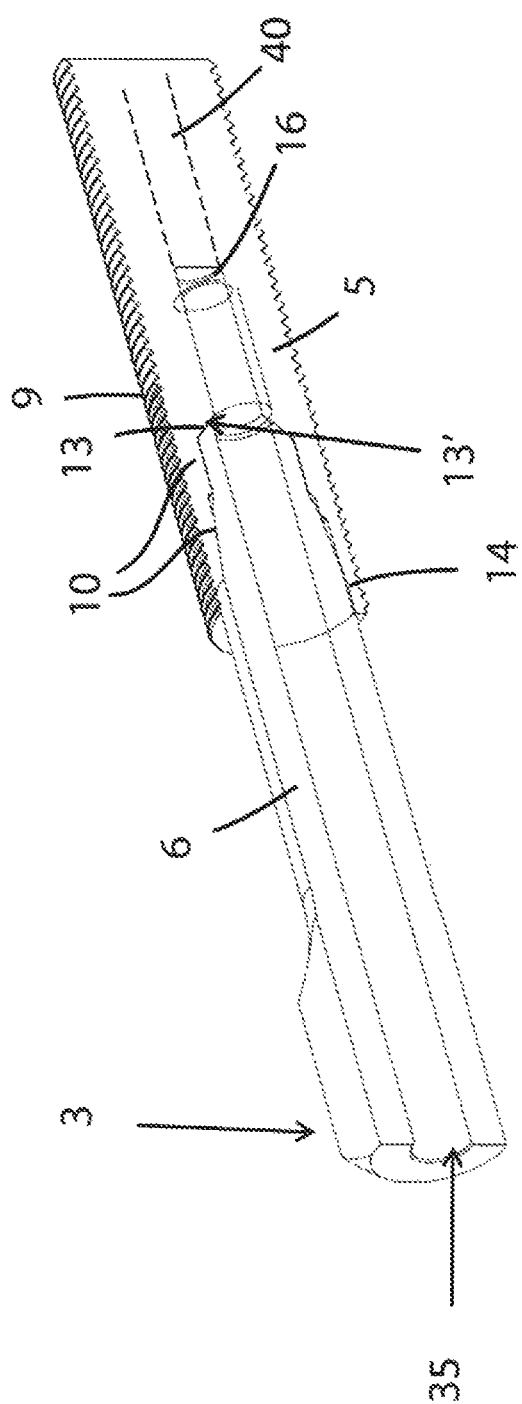
FIG. 2 is a schematic view illustrating an embodiment of the invention having a cylindrical press-fit.
Figure 3:
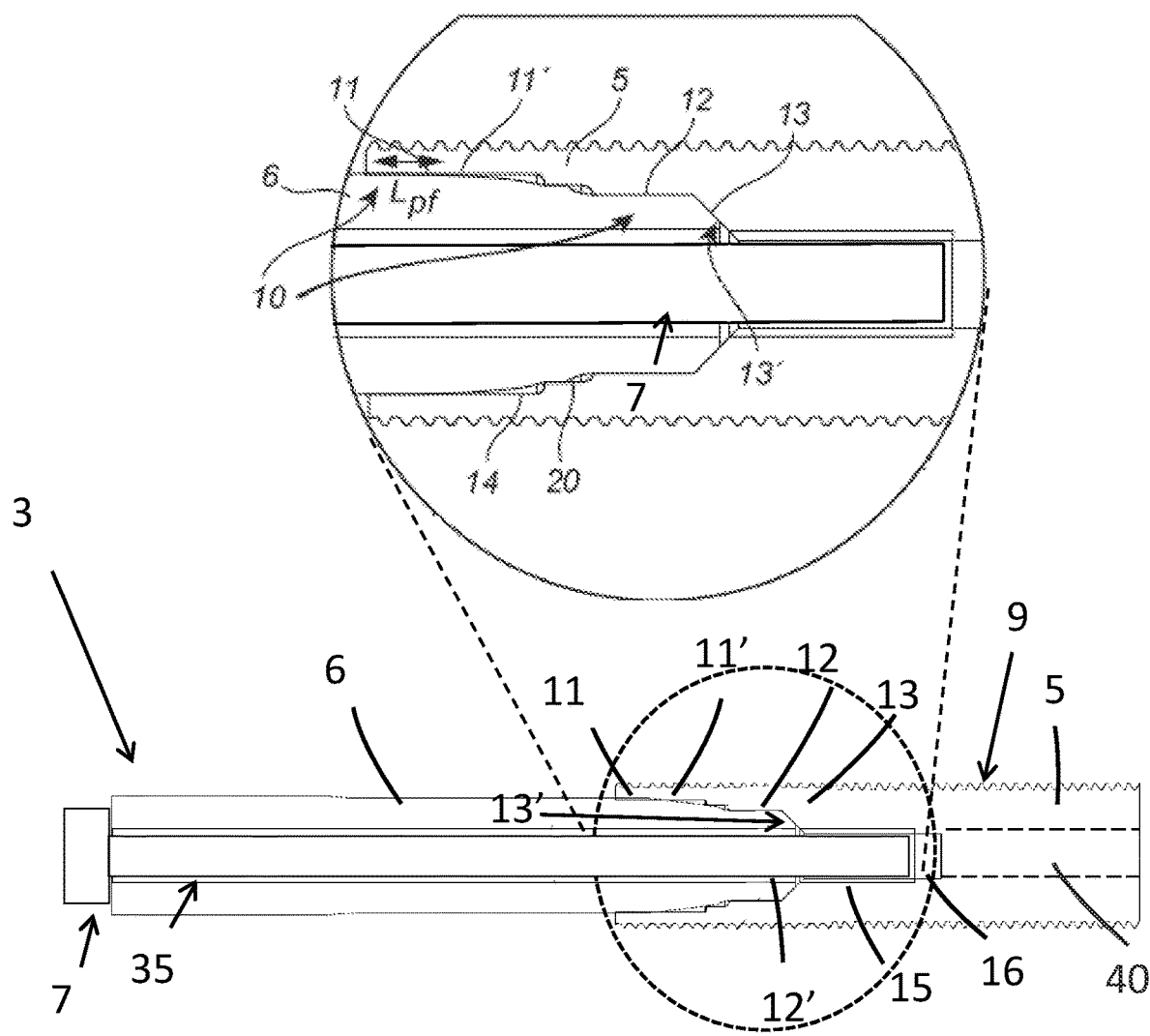
FIG. 3 is a schematic view illustrating more in detail the connection between an anchoring element and an abutment with a cylindrical press-fit.

FIG. 2 and FIG. 3 are schematic cross-sectional views of a preferred embodiment of the invention. FIG. 2 and FIG. 3 show the anchoring element, also known as a fixture 5, comprising an outer threaded profile 9 for anchoring to bone tissue of a human body. There is further shown in an abutment 6 comprising a distal portion 3 for linking the anchoring system to an external prosthetic component. A connection area 10 of the fixture 5 comprises a press-fit 11(11') (shown in FIG. 3), an anti-rotational geometry 12 (e.g. hexagon or other geometrical shape such as triangle, rectangle, square etc) shown in FIG. 3, and a conical portion 13 at the bottom of the anti-rotational geometry forming an additional mating surface for the abutment 6, best seen in FIG. 3. With further reference to FIG. 3, the conical portion 13' of the abutment and the corresponding conical portion 13 on the fixture 5 provide a secure and stable contact interface of the proximal end of the abutment 6 to the anchoring element 5. In other words, the conical portion 13 of the fixture 5 and the corresponding mating conical portion 13' of the abutment 6 provide a stable contact point at the most proximal end of the connection area 10 for the abutment 6. The press-fit 11 is located in the most distal part of the through hole 16, at the opening 14 of the fixture 5.

In addition, as shown in FIG. 3, the connection area 10 in the through-hole 16 comprises fastening means in the form of inner threads 15 for the abutment screw 7. There is further an inner portion 40 of the through hole 16 used as a pathway for communication or transmission of biological and physical parameters. The inner portion 40 in the through hole 16 is located on the proximal side of the inner threads 15 and is schematically indicated by dotted lines. The optional inner portion 40 may be sealed by a central screw (not shown). The abutment screw 7 is arranged through the axial through-hole 35 ranging through the abutment 6 in the proximal-distal direction and is fastened at the inner threads 15 for fastening the abutment 6 to the fixture 5.

Figure 4:
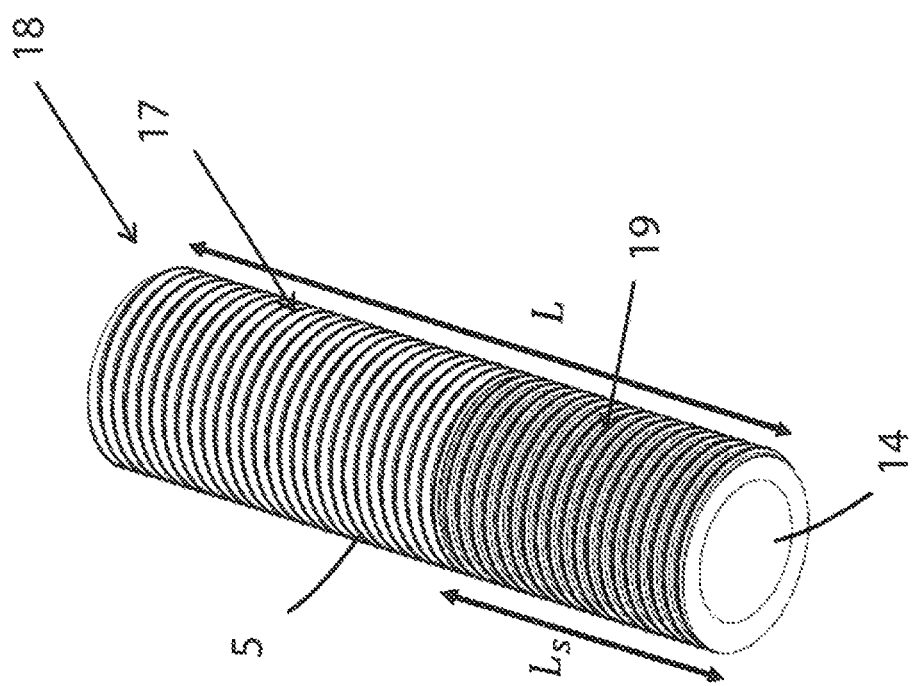
FIG. 4 illustrates the outer profile of an anchoring element according to an exemplary embodiment of the invention.

As illustrated more in detail in FIG. 4 the anchoring element 5 (i.e. the fixture) has a threaded outer profile of two different thread profiles in this exemplary embodiment. Specifically, the total length L of the fixture is divided into a first portion 17 with a deeper thread depth in the proximal portion 18 of the fixture 5 to improve the bone anchoring surface area. The distal, second portion 19 has a shallower thread depth to increase the wall thickness ($t_w$) of that portion of the fixture 5 thus increasing the mechanical strength in the second portion 19 substantially. In this exemplary embodiment, the length of the portion 19 with the shallower thread $L_s$ is defined by the inner geometry of the fixture.

Figure 5:
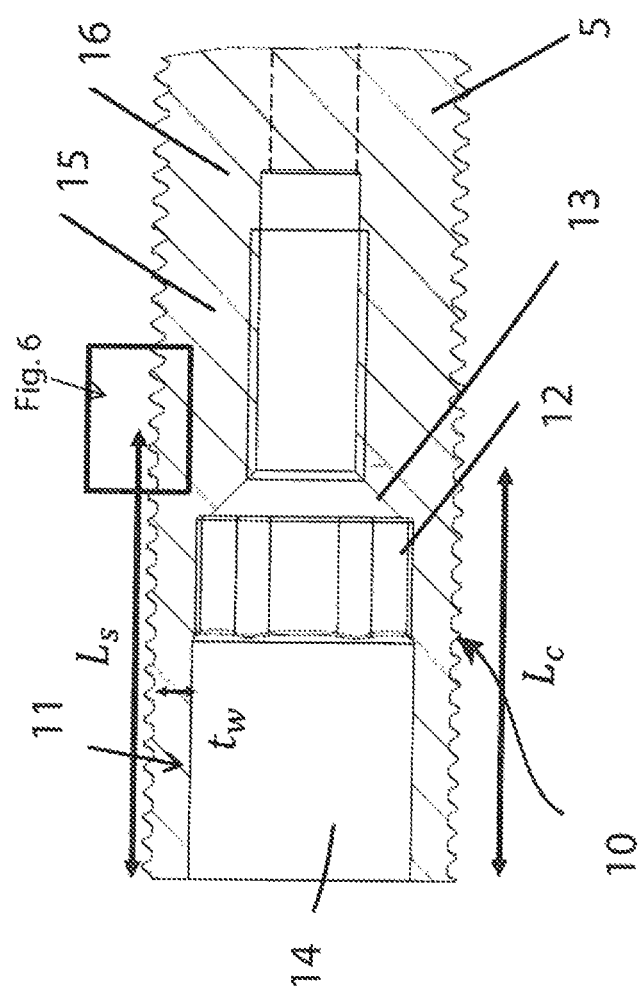
FIG. 5 illustrates in more detail the inner profile of a first embodiment of the anchoring element according to FIG. 2 having a cylindrical press-fit.

As illustrated in FIG. 5 the length $L_s$ of the second portion 19 covers more than the total length $L_c$ of the mating geometry (comprising the press-fit portion 11, the anti-rotation geometry 12 and the conical portion 13) to improve the wall thickness and thus increasing the strength of the distal portion of the fixture 5. FIG. 5 illustrates a schematic partial cross-section of an anchoring element 5 comprising a conical portion 13, an anti-rotation geometry 12, a connection area 10 having length $L_c$, a (cylindrical) press-fit portion 11, inner threads 15 adapted to receive and engage with an abutment screw 7 (see FIG. 10).

Figure 6:
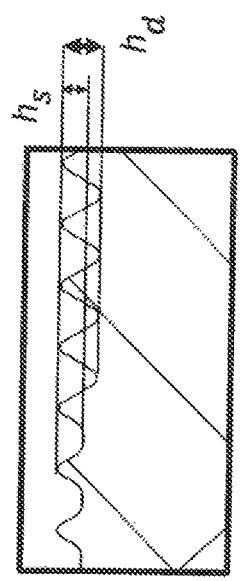
FIG. 6 is an enlarged view of the thread profiles illustrating the difference in thread depth between the deeper threads and the shallow threads.

FIG. 6 is an enlarged view of the thread profiles. The difference in thread depth Δh between the deeper thread $h_d$ and the shallow thread $h_s$ is in this example set between an interval as indicated in Table 1 in FIG. 11.

The distal part of the inner profile of the fixture 5 is the female portion of the connection between the fixture 5 and the abutment 6, where the abutment 6 is the male part of the connection. The fixture 5 and the abutment 6 are retained by an abutment screw 7 shown in FIG. 10, which goes through the through-hole 35 (see e.g. FIG. 2 or 3) of the abutment 6 and is fastened in the fixture by fastening means in the form of the inner threads 15 or the like.

Figure 9:
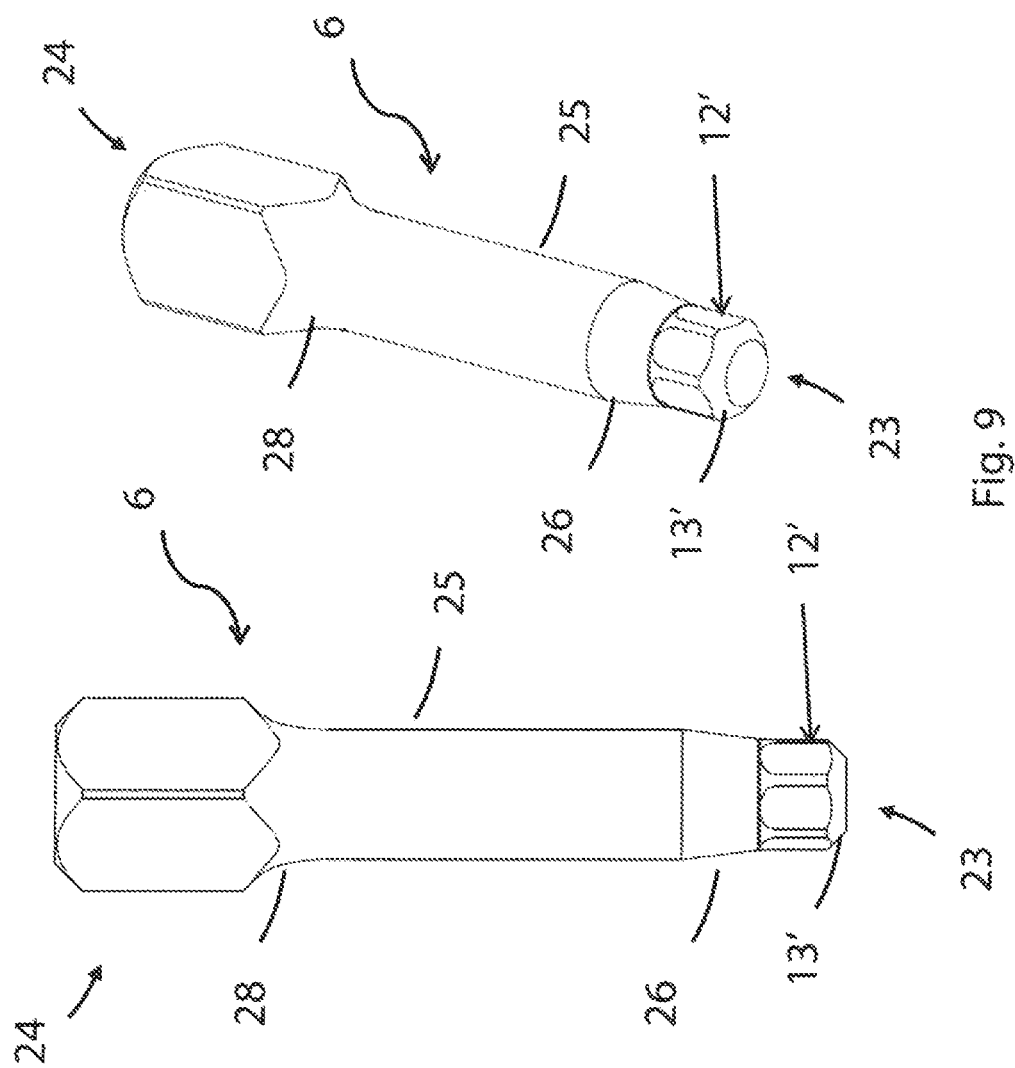
FIG. 9 illustrates two views of an exemplary abutment for the anchoring system.

With further reference FIG. 3 and FIG. 5 in conjunction with FIG. 9, where FIG. 9 shows two views of an abutment 6 according to an embodiment of the invention, the anti-rotational geometry 12' of the abutment is used for installation in surgery but also acts as an anti-rotational safety function as the fixture 5 (FIG. 3 or 5) has geometrically mating part. In addition, and also with reference to FIG. 3 or 5, the connection area 10 comprises a conical surface 13 forming an additional mating surface for the abutment 6, for improving load distribution (due to an increased distance between contact points) and stability of the abutment. The connection area further comprises a cylindrical press-fit 11 (11') at the most distal part of the connection area, illustrated in e.g. FIG. 3. The length of the press-fit $L_{pf}$ has been increased compared to previous connection geometries. As indicated in the table in FIG. 11 $L_{pf}$ could be 2-15 mm for a typical fixture length of 60-100 mm.

Figure 7:
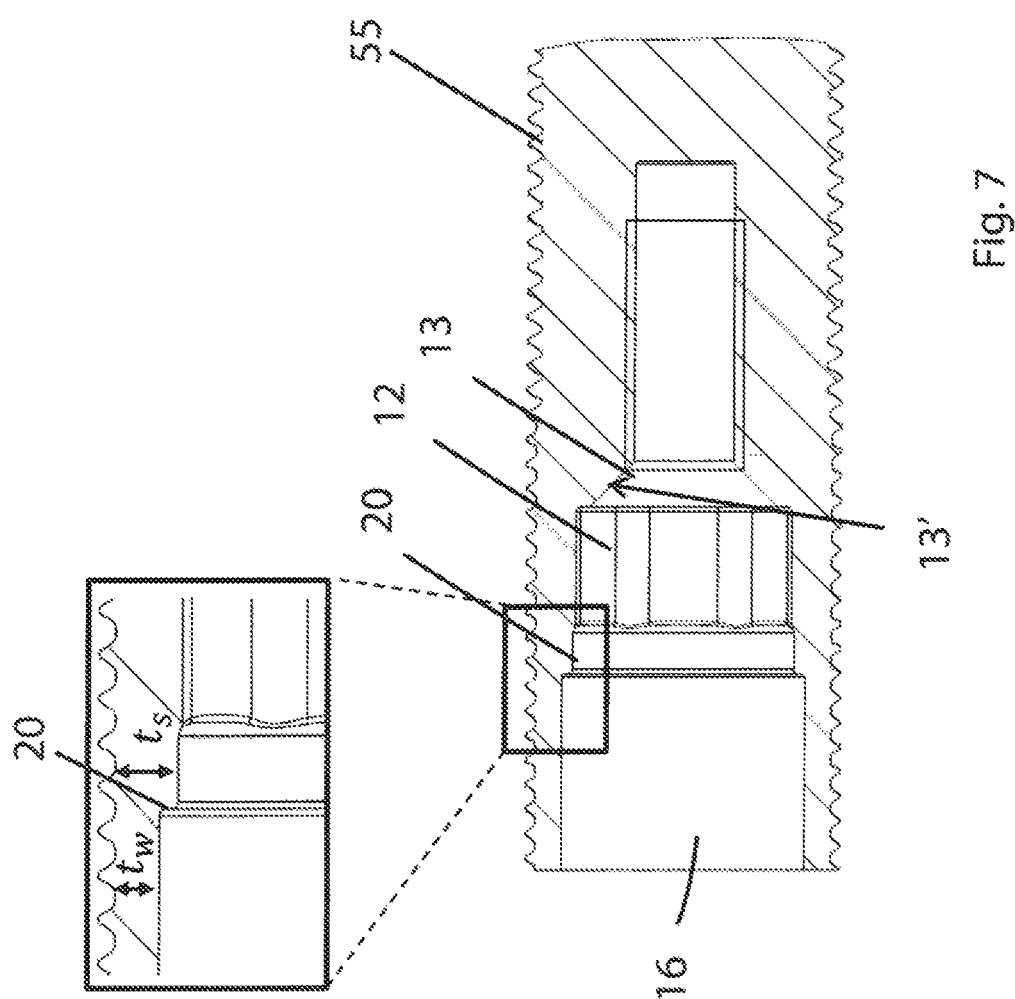
FIG. 7 illustrates an alternative to the embodiment illustrated in FIG. 5 in which the diameter of the distal inner hole of the fixture has a step where the wall thickness has been increased.

Referring now to FIG. 7, as an alternative to the embodiment illustrated in FIG. 5 the diameter of the distal portion of the through-hole 16 of a fixture 55 may have a step 20 with a larger wall thickness $t_w$ has been compared to the adjacent portion. The increased wall thickness $t_s$ due to the step 20 will help to gradually increase the strength of the fixture. As illustrated in the table in FIG. 9 the increased wall thickness $t_s$ might be in the interval of 1 $t_w$–2 $t_w$. Due to the described outer and inner profile it has been possible to increase the diameter of the inner through hole in the fixture to allow for a larger diameter abutment.

Figure 8:
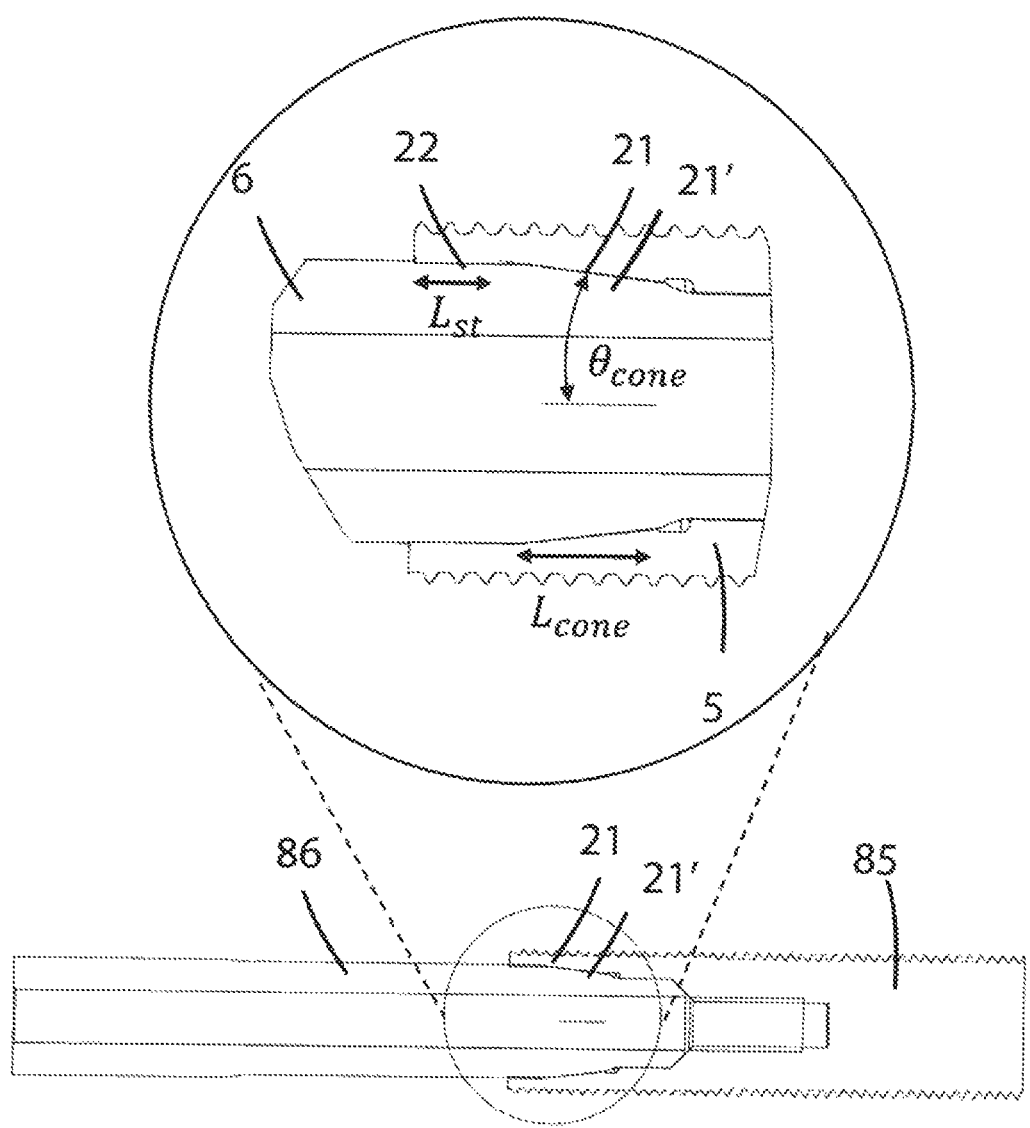
FIG. 8 is a schematic view illustrating an embodiment of the invention having a conical press-fit.

FIG. 8 discloses another embodiment of the invention. In FIG. 8 there is shown, as an alternative to the design with the cylindrical press-fit, a conical press-fit 21 having a the cone angle $\theta_{cone}$ and a cone length $L_{cone}$, see example parameters in the table in FIG. 9. The straight portion 22 at the distal most end of the fixture 85 acts as a stress relief to avoid high stress singularities and has a length $L_{st}$ where $L_{st}$ is less than the length of the cone $L_{cone}$. The abutment 86 comprises a corresponding conical press-fit portion 21'.

The inner surface of the connection area 10 in the fixture 5, either with a cylindrical or a conical press-fit 11, 21 could be treated with surface treatments known in the art, such as burnishing, Diamond-like-Carbon (DLC) coating, nitriding, etc, in order to enhance wear resistance.

As already mentioned the abutment 6 (86) is the link between the anchoring system and the prosthesis and it is the male part of the connection described above. FIG. 9 illustrates an example of an abutment for the anchoring system, having a proximal portion 23, a distal portion 24 and an intermediate longitudinal stem 25. The distal portion 24 has a geometrical form, such as square, hex, sphere, cylinder, etc, and acts as a connection to a safety device which is connected to the actual prosthesis. The geometry of the conical surface 26 is to accommodate to a press-fit with a cylindrical as well as a conical design. A conical portion 13' at the most proximal end of the abutment provides for stability and load distribution when mated with a corresponding conical portion 13 of an anchoring element 5. The conical portion 13' of the abutment and the corresponding mating conical portion 13 of the anchoring element 5 provides a stable contact point at the most proximal end of the connection area 10 (see above description of connection area), compared to for example flat to flat surface connections. The interface 28 between the cylindrical stem 25 and the geometrical distal portion 24 has radiuses of different sizes to act as stress relief for stress concentrations in that area. The surface of the abutment could be treated with special surface treatments known in the art, such as Nitride diffusion, Diamond-like-Carbon (DLC) coating, Physical Vapor Deposition (PVD) coating, etc, to reduce wear and increase fretting resistance properties in the connection area.

Figure 10:
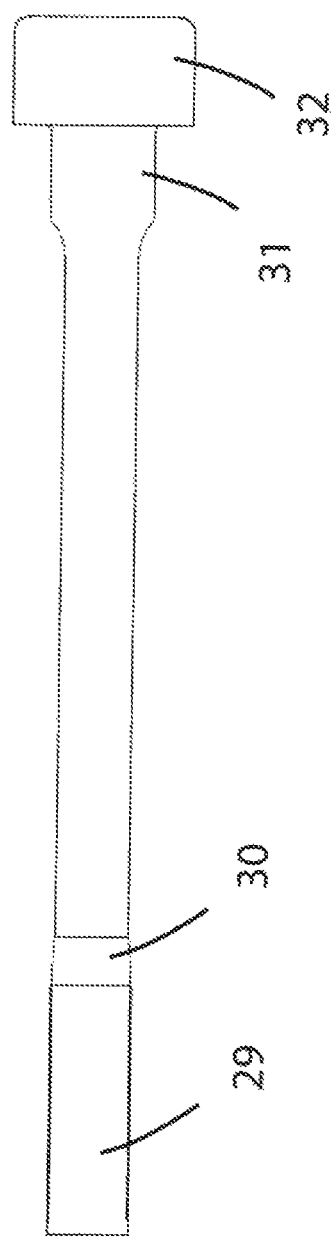
FIG. 10 is an example of an abutment screw for the anchoring system.

FIG. 10 is an example of an abutment screw for the anchoring system. The screw is used as a retention mechanism between the fixture and the abutment. The screw has rolled formed threads 29 at the proximal end accommodated to the inner threads 15 in the fixture. The screw has a slight conical portion 30 next to the threads 29 and an increased diameter portion 31 is provided under the screw head 32 that strengthens the design in that region for avoiding fractures. At least the threads 29 and the increased diameter portion 31 are preferably surface treated (e.g. DLC coating) after machining to provide a lower friction coefficient. In some implementations the entire abutment screw is surface treated.

The table in FIG. 11 indicates preferred design parameters intervals for the invention.

In addition, variations to the disclosed embodiments can be understood and effected by the skilled addressee in practicing the claimed invention, from a study of the drawings, the disclosure, and the appended claims. For example, it should be understood that the invention is not limited to femur bone and limb prostheses but could be used for other types of long bones in the human body. Furthermore, in the claims, the word "comprising" does not exclude other elements or steps, and the indefinite article "a" or "an" does not exclude a plurality.

The invention claimed is:

1. A anchoring system for attaching a prosthesis to a human body, said anchoring system comprising:
    an anchoring element comprising an outer threaded profile for anchoring to bone tissue of the human body,
    an abutment comprising a distal portion for linking the anchoring system to an external prosthetic component,
    an abutment screw for attaching the abutment to the anchoring element for providing a mechanical connection between the anchoring element and the abutment,
    wherein, said anchoring element comprises a through-hole having an opening with an inner profile for providing a connection area for the abutment,
    said connection area comprising a press-fit portion in a distal portion of said connection area, said press-fit portion having an opening dimension smaller than a dimension of a press-fit portion of said abutment such that said abutment is attached to said anchoring element in the connection area by a press-fit connection, wherein
    said connection area comprises an anti-rotation geometry proximal to the press-fit portion, said abutment comprising a corresponding mating anti-rotation geometry proximal to said press-fit portion of said abutment configured to engage with the anti-rotation geometry of said anchoring element, and wherein
    said connection area comprises a conical portion proximal to the anti-rotational geometry forming a mating geometry for a corresponding conical portion of the abutment.

2. The anchoring system according to claim 1, wherein the outer threaded profile of the anchoring element comprises:
    a first thread portion with a first thread depth ($h_d$), and
    a second thread portion with a second thread depth ($h_s$),
    wherein the first thread depth is larger than the second thread depth, and wherein the first thread portion is arranged in a proximal portion of the anchoring element and the second thread portion is arranged in a distal portion of the anchoring element.

3. The anchoring system according to claim 2, wherein the first thread portion and the second thread portion extend over an entire total length from a proximal-most end to a distal-most end of the anchoring element.

4. The anchoring system according to claim 2, wherein the second thread portion extends over a length (Ls) from the distal portion to beyond the connection area.

5. The anchoring system according to claim 1, wherein the press-fit portion of the connection area extends from a distal-most end of the distal portion of the anchoring element and in a proximal direction.

6. The anchoring system according to claim 1, wherein the press-fit portion of the connection area is cylindrical.

7. The anchoring system according to claim 6, wherein a length of the press-fit portion is in the range of 2 to 15 mm.

8. The anchoring system according to claim 1, wherein the press-fit portion of the connection area is conical.

9. The anchoring system according to claim 8, wherein a cone angle of the conical press-fit portion is in the range between 0.2° to 30°.

10. The anchoring system according to claim 8, wherein the connection area comprises a straight portion arranged on a distal-most part of the connection area adjacent to the conical press-fit portion.

11. The anchoring system according to claim 10, wherein a length of the straight portion is less than a length of the conical portion.

12. The anchoring system according to claim 1, wherein the anti-rotation geometry has a polygon cross-section.

13. The anchoring system according to claim 1, wherein mating surfaces between the anchoring element and the abutment have been surface treated for providing wear and fretting resistance properties for the anchoring element and the abutment.

14. The anchoring system according to claim 1, wherein a cone angle of the conical portion of the abutment is in the range of 25° to 65°.

15. The anchoring system according to claim 1, wherein a cone angle of the conical portion of the abutment is about 45°.

16. The anchoring system according to claim 1, wherein the abutment comprises a through-hole in a proximal-distal direction, wherein for retaining the abutment to the anchoring element the abutment screw is arranged through the through-hole and fastened to inner threads in the anchoring element.

* * * * *